United States Patent [19]

Van Peppen et al.

[11] 4,164,515

[45] Aug. 14, 1979

[54] PRODUCTION OF CYCLOHEXANONE

[75] Inventors: Jan F. Van Peppen; William B. Fisher, both of Chester, Va.

[73] Assignee: Allied Chemical Corporation, Morris Township, Morris County, N.J.

[21] Appl. No.: 853,720

[22] Filed: Nov. 21, 1977

[51] Int. Cl.² .................... C07C 27/00; C07C 29/20; C07C 45/00
[52] U.S. Cl. .................. 260/586 P; 568/835
[58] Field of Search .................. 260/586 P; 568/835

[56] References Cited

U.S. PATENT DOCUMENTS

| | | | |
|---|---|---|---|
| 2,760,940 | 8/1956 | Schwarzenbek | 252/466 |
| 2,777,805 | 1/1957 | Lefrancois et al. | 196/50 |
| 2,829,166 | 4/1958 | Joris et al. | 260/586 P |
| 2,857,337 | 10/1958 | Hamilton et al. | 252/472 |
| 2,857,432 | 10/1958 | Joris | 260/586 P |
| 2,873,296 | 2/1959 | Nilsson et al. | 260/586 P |
| 3,076,810 | 2/1963 | Duggan et al. | 260/586 P |
| 3,187,050 | 6/1965 | Duggan et al. | 260/586 P |
| 3,305,586 | 2/1967 | Phielix | 260/586 P |
| 3,500,028 | 3/1970 | Killian | 235/183 |
| 3,542,863 | 11/1970 | Zimmerschied | 260/525 |
| 3,692,845 | 9/1972 | Cheema et al. | 260/621 A |
| 3,798,002 | 3/1974 | Putman | 23/253 A |
| 3,809,621 | 5/1974 | Putman | 202/205 |
| 3,959,382 | 5/1976 | Yeh et al. | 260/586 P |
| 3,965,187 | 6/1976 | Little et al. | 260/586 P |

FOREIGN PATENT DOCUMENTS

| | | | |
|---|---|---|---|
| 892187 | 2/1972 | Canada | 260/586 P |
| 2163362 | 7/1972 | Fed. Rep. of Germany . | |
| 2357370 | 5/1974 | Fed. Rep. of Germany . | |
| 2619660 | 11/1976 | Fed. Rep. of Germany . | |

OTHER PUBLICATIONS

"Chemical Eng. Handbook", John Perry Editor, 4th Edition (1963), pp. 22-1-22-3, 22-54-22-75, McGraw Hill Book Co., Inc.

*Primary Examiner*—Norman Morgenstern
*Attorney, Agent, or Firm*—Fred L. Kelly; Richard A. Anderson

[57] ABSTRACT

A computer controlled process for preparation of cyclohexanone by liquid phase, catalytic hydrogenation of phenol in three or more hydrogenation stages by using a computer control system interrelated with a phenol hydrogenation system in such a manner that it is capable of correlating a predetermined mole ratio of phenol to cyclohexanone with a predetermined maximum temperature in each of the hydrogenation stages, whereby intrinsic safety of operation is achieved by operating at temperatures at or below the atmospheric boiling point in each reactor.

12 Claims, No Drawings

PRODUCTION OF CYCLOHEXANONE

CROSS REFERENCES TO RELATED APPLICATIONS

This application is related to U.S. applications Ser. No. 527,466 filed Nov. 26, 1974, Ser. No. 667,760 filed Mar. 17, 1976, Ser. No. 667,735 filed Mar. 17, 1976, Ser. No. 793,563 filed May 4, 1977, U.S. Pat. No. 4,092,360, Ser. No. 815,397 filed July 13, 1977 now abandoned and Ser. No. 827,189 filed Aug. 23, 1977.

BACKGROUND OF THE INVENTION

This invention relates to preparation of cyclohexanone by hydrogenation of phenol; more particularly, it relates to a computer controlled process for preparation of cyclohexanone by liquid phase, catalytic hydrogenation of phenol in three or more hydrogenation stages.

In the hydrogenation of phenol employing a palladium catalyst, the activity of the catalyst, and hence the rate of hydrogenation, decreases with continued use of the catalyst due to impurities present in the hydrogenation reaction mixture which poison the catalyst. While processes, such as those disclosed in U.S. Pat. Nos. 3,692,845 and 3,187,050, have been developed to purify organic compounds such as phenol to be hydrogenated, the poisoning of metallic catalysts has not been entirely eliminated in large scale commercial processes due to long term accumulation of impurities, particularly impurities which are produced during the processing.

To avoid the economically prohibitive alternatives of discarding poisoned catalyst or continuing to use the poisoned catalyst at a reduced rate of hydrogenation, it is known to promote the rate of hydrogenation, thereby at least partially overcoming the disadvantages of continued use of such poisoned palladium catalysts. The hydrogenation of phenol to cyclohexanone is normally promoted by the use of "promoted palladium-on-carbon catalysts", i.e., catalysts which have been treated prior to their addition to the hydrogenation reaction mixture, to incorporate on the catalysts a material which enhances the activity of the catalysts. Thus, in U.S. Pat. No. 3,076,810, cyclohexanone is produced by hydrogenating phenol using a sodium-promoted palladium catalyst which has been modified prior to its introduction to the reaction mixture to incorporate sodium thereon. Alkaline reacting agents in limited amounts are also disclosed as being added to assist in promotion when the sodium-promoted catalyst is employed.

U.S. application Ser. No. 815,397, filed July 13, 1977, discloses a highly active catalyst for selective hydrogenation of phenol to cyclohexanone which comprises 0.2 to 10 weight percent of palladium, based on the total weight of the catalyst, supported on carbon particles having diameters of 3 to 300 microns and a surface area of 100 to 2000 $m^2$/gram, said catalyst being promoted by sodium in an amount of at least 1000 ppm. Preferably, said sodium-promoted palladium catalyst is additionally promoted during said hydrogenation by contacting the catalyst with phenol containing a small amount of an in situ promoter selected from the group consisting of sodium hydroxide, sodium carbonate, and sodium phenate, said amount being 10 to 300 ppm in terms of sodium of said in situ promoter.

The highly active catalyst of U.S. application Ser. No. 815,397 is an important contribution to this art because it permits hydrogenation of phenol with reduced amounts of catalyst and with intrinsic safety by operating at temperatures at or below the atmospheric boiling point of the reaction mass. However, we have found that control of the hydrogenation reaction is difficult with use of the highly active catalyst, and research has been continued to develop a computer controlled process.

SUMMARY OF THE INVENTION

According to the present invention, there is provided a computer controlled process for producing cyclohexanone by liquid phase hydrogenation of phenol in the presence of a sodium-promoted palladium-on-carbon catalyst, including a control system for controlling the ratio of phenol to cyclohexanone in the reaction mixture and limiting the maximum reaction temperature during hydrogenation reaction stages in three or more reactors in series, comprising:

(a) generating and storing in the computer sampled data inputs from each reactor of analog representations of reactor hydrogen pressure, temperature, phenol concentration, cyclohexanone concentration, catalyst concentration, hydrogen feed rate, phenol feed rate and cyclohexanone flash rate;

(b) processing said sampled inputs in the computer by relating them to a stored anticipatory control program to provide output data for controlling the ratio of phenol to cyclohexanone and limiting the maximum reaction temperature during the hydrogenation reaction stages; and (c) controlling the ratio of phenol to cyclohexanone and limiting the maximum reaction temperature during said hydrogenation reaction stages in response to said output data from the computer, the process being further characterized in that the reaction temperature is maintained at or below the atmospheric boiling point of the reaction mixture in each reactor.

DESCRIPTION OF THE PREFERRED EMBODIMENT

The preferred process of the present invention provides a computer controlled process for producing cyclohexanone comprising hydrogenating phenol by passing hydrogen in contact with phenol in the presence of a sodium-promoted palladium-on-carbon catalyst at a temperature of 135° C. to 184° C., said catalyst being further characterized in that it is composed of palladium coated carbon particles, said carbon particles having diameters of 3 to 300 microns and a surface area of 100 to 2000 $m^2$/gram, said phenol containing a small amount of an in situ promoter selected from the group consisting of sodium hydroxide, sodium carbonate and sodium phenate, said amount being 10 to 300 ppm in terms of alkali metal of said in situ promoter. Respecting safety of operation, it is important that the present process provides controlled hydrogenation of phenol in the liquid phase in a series of reactors with each reactor maintained at or below the atmospheric boiling point of the reaction mixture in the reactor.

In one preferred embodiment of the present invention, 3 to 5 reactors are connected in series arrangement for hydrogenation of the phenol to cyclohexanone. Each reactor has adjustable means such as an air-operated diaphragm control valve for adjusting the hydrogen feed rate and setting the hydrogen pressure therein, whereby the rate of hydrogenation in each reactor can be controlled. A portion of the cyclohexanone formed in each reactor is taken overhead as vapor, condensed, and separated. For convenience, this vaporized portion of the cyclohexanone may be called "cyclohexanone flash". A computer is provided and is associated with the reaction so as to control the mole ratio of phenol to cyclohexanone of the reaction mixture exiting from each reactor. The maximum reaction temperature in each reactor is limited by the computer based on the mole ratio of phenol to cyclohexanone in the reaction mixture. Table 1 indicates the preferred maximum reaction temperature for various mole ratios of phenol to cyclohexanone in the reaction mixture.

TABLE 1

| Reaction Mole Ratio of Phenol to Cyclohexanone | Maximum Reaction Temperature, °C. |
| --- | --- |
| 90/10 | 182.0 |
| 80/20 | 184.0 |
| 70/30 | 184.0 |
| 60/40 | 181.0 |
| 50/50 | 177.0 |
| 40/60 | 172.5 |
| 30/70 | 168.0 |
| 20/80 | 164.0 |
| 10/90 | 159.0 |
| 5/95 | 158.0 |

Analog inputs for the computer are derived from means such as chromatographic means for sensing the concentration of phenol and cyclohexanone in the reaction mixture from each reactor, and means for sensing temperature of the entering reaction mixture and of the exiting reaction mixture at each reactor. "Feedforward" (i.e., anticipatory control) and feedback algorithms of known form (in particular proportional, integral, derivative) are used to provide control of phenol to cyclohexanone mole ratio operative to hold the final mole ratio of phenol to cyclohexanone within 0.5 percent variation.

A control system including the computer operates in a closed loop to maintain "target" hydrogen pressure set points, as determined by the computer for each reactor. Additionally, target set points or control limits are set in the computer for catalyst concentration and/or phenol feed rate and cyclohexanone flash rate.

At intervals frequent enough to provide close monitoring, the direct digital control system (DDC) of the computer evaluates ratio of phenol to cyclohexanone for each reactor. The currently existing ratio is compared to the desired ratio. A new pressure set point and corresponding hydrogen feed rate is practically instantaneously calculated by the computer and corresponding signals are generated and actuate the hydrogen pressure control means on the reactor.

The computer has means for accepting analog input signals; means for generating analog output signals; a real time clock or scheduler; and means for feeding and storing an anticipatory control program in the computer. The control system includes means for generating analog input samples representing at least hydrogen pressure, mole ratio of phenol to cyclohexanone and temperature for a reactor; and the computer has storing means for storing the analog input samples, a central processor for processing the analog input samples by relating the samples to the anticipatory control program, and means described more fully below for controlling the reaction within the predetermined limits of the anticipatory control program by use of signals from the computer responsive to the analog input samples. Associated with the controlling means is an alarm and/or lock-in means to give warning and/or to stop the computer and/or to take a variable off control in the event of a malfunction.

The computer is also provided with such conventional hardware as a multiple word disc, an input/output teletype, and contact closures.

A basic element of the computer control system is the real time clock or scheduler. This provides executive control for running analog inputs sampling, analog outputs, audio alarms, digital filtering and limit checking of control variables. A first portion of the scheduler maintains master control of the time dependent events by a supervising routine. Events scheduled at intervals measured in seconds, and time dependent operations, are executed immediately. Operations scheduled at intervals of minutes are placed in a queue table for execution as time permits. A second non-time dependent portion of this scheduler is designed to provide linkage for programs residing on a supplementary disc drive. As time permits the scheduler calls the appropriate program from disc into variable core and executes the program in the background mode.

Encompassed within the overall control logic of the scheduler is the analog input driver used to sample process variables at specified intervals. Each input may have varying sampling intervals.

Another section of the analog input module is to digitally filter raw analog input data. This is accomplished by a numerical approximation to a first order lag filter.

A third section of the analog input module is to check all controlled variables against a specified set of lower and upper limits. Hard copy messages and audio alarms are activated by this portion of the system upon violation of the predetermined limits.

Also run by the real time clock or scheduler is the analog output module and its process control subcomponents. The functions of this module are to maintain the direct digital control ("DDC") error history and to calculate new set point adjustments for the process control subcomponents by solving the velocity form of proportional, plus integral, plus derivative ("PID") mode control equations. In addition, it supplies the digital-to-analog converters with appropriate data for maintaining process conditions on the reactors by direct interface to control values.

The "feedforward" adjustments to be implemented by the process control subcomponents are calculated from an algorithm of the form:

$$PADJ = C*\Delta R \qquad (1)$$

where:
* indicates multiplication;
PADJ = Adjustment to the pressure set point for the reactor;
C = Constant
$\Delta R$ = Change of mole ratio of phenol to cyclohexanone since last feedforward implementation.

The "feedback" adjustments are calculated from an algorithm of the form:

$$PADJ = PN - PCSET$$

PN is calculated by the following algorithm:

$$PN = (PN-1) + K*[EN - (EN-1)] + KI*T*EN + KD*[EN - 2(EN-1) + (EN-2)]/T \qquad (2)$$

where:
* idicates multiplication;
PN, (PN−1) are the set points calculated currently and that last previously calculated;
PADJ is the adjustment to the pressure set point; EN, (EN−1), (EN−2) are the error terms measured currently and at last two previous measurements (i.e., at time intervals N, N−1 and N−2) for mole ratio of phenol to cyclohexanone of reaction mixture exiting from the reactor;
KI is the integral time constant for the given reactor;
KD is the derivative time constant for the given reactor;
T is the time interval between execution of a supervisory routine,
PCSET is the currently existing hydrogen pressure set point.

The DDC operation is scheduled at a time interval specified by the real time clock or scheduler. The computer checks to see if it is time to implement feedforward control and takes the appropriate action. The computer then updates the error table and calculates a new value for PN based on the above algorithm (1). It then checks for feedback implementation time and outputs an adjustment if necessary. Adjustments are transmitted to the process control subcomponents for implementation. All computer initiated process changes are reflected on the teletype located in the control room.

The second non-time dependent portion of the real time clock or scheduler handles operations which may be delayed and executed as time permits. This portion of the real time system is responsible for the following system operations: (1) execute programs in variable core (background) by servicing the queuing table; (2) output to the teletype all hardware and system error messages; (3) take data from the disc buffer and output it to the teletype; (4) run the operations console program from the disc; (5) handle all disc I/o requests which may be data or programs; (6) establish need to allow complete priority changes, i.e., all changes to protected areas of core which would affect process control functions; and (7) run events 1–6 in such a manner as not to conflict with each other or demote the time dependent operations.

Additional portions of the real time clock or scheduler set time schedules and priority of handling, by "interrupt servicing routines", for each of the hardware devices. These include the real time clock, disc, teletype I/o, emergency timer, and digital outputs.

The limit checking program is a disc resident program. The computer automatically brings the limit program into core for execution at an interval specified by the user. The function of this program is to check the current status of each input variable. In order to accomplish this, the program converts the filtered analog input to engineering units and then proceeds to check variable upper and lower limits. If a variable is outside this range, the computer automatically takes the variable off computer control and an alarm is actuated.

The normal execution interval is 3 minutes to 5 minutes as set but may vary depending upon the requirements. Hard copy of all limit violations is provided with respect to variable number, data, time and actual value of the variable.

Each portion of the system includes alarm means and/or lock-in means to alert the process operator to a malfunction and/or restrict computer operations in the event of failure. The alarm/lock-in means is activated when the computer fails to provide the periodic signal necessary to repeatedly reset an emergency or watchdog timer. In the event of a computer failure (e.g., computer "looping"), the audio alarm will sound; at the same time the DDC control system is locked to the last previous settings.

Likewise, in the event of violations of predetermined limits upon the process variables being monitored, or failures to provide an input signal at the scheduled time for such variable, the alarm is sounded and messages are printed out, which tell the operator which process variable is in error; and such variable is automatically taken off control.

The alarm and/or lock-in means are actuated by an emergency or watchdog timer. As part of the computer program, the timer is set for 5 seconds by a signal from the computer; and must be reset by such signal within this interval to prevent its actuating the alarm. Unless the timer is so reset, the alarm and/or lock-in means is actuated; and/or the computer stops operating, and the last previous setting is locked in until the operator takes control or reactivates the computer control.

The present invention is further illustrated by reference to the following examples wherein parts and percentages are by weight unless otherwise indicated.

EXAMPLE 1

This example demonstrates the feasibility of continuously operating the liquid phase hydrogenation process of the present invention.

The first of a series of three agitated hydrogenation vessels is charged with about 45,700 parts per hour of phenol, 1.3 to 2.0 parts of sodium carbonate, and 1,200 parts per hour of a sodium-promoted, palladium-on-carbon catalyst having a sodium content of 0.25–0.40 percent, said catalyst containing about 0.93 percent palladium on carbon particles having diameters of about 5 to 100 microns and a surface area of about 1000 m$^2$/gram. About 67 percent of the palladium on the catalyst is present as elemental palladium. Each hydrogenation vessel is connected in series so that the reaction mixture flows through the three vessels in about 2 hours, the hydrogen being charged to the first vessel. Each reactor has adjustable means such as an air operated adjustable valve for setting the hydrogen pressure therein, whereby the hydrogenation reaction may be automatically controlled by means of a computer control system. A portion of the cyclohexanone formed in each reactor is taken overhead as vapor, condensed, and separated. This portion of the cyclohexanone may be called "cyclohexanone flash".

The computer control system provides efficient hydrogenation in each reactor while maintaining maximum safety of operation. Briefly stated, a digital computer controls the mole ratio of phenol to cyclohexanone exiting from each reactor and simultaneously limits the maximum reaction temperature in the reactor, so that intrinsic safety of operation is achieved by operating at temperatures at or below the atmospheric boiling point of the reaction mixture in each reactor. For maximum efficiency, the reaction temperature in each reactor is maintained at 0° to 5° C. below the atmospheric boiling point of the reaction mixture in the reactor. As discussed above, the atmospheric boiling point of the reaction mixture drops significantly as the reaction proceeds through the series of reactors.

By conventional means, sampled data inputs from each reactor of analog representations of reactor hydrogen pressure, temperature, phenol concentration, cyclohexanone concentration, catalyst concentration, hydrogen feed rate, phenol feed rate and cyclohexanone flash rate are generated and stored in the computer. Analog inputs for the computer are derived from means such as chromatographic means for sensing the concentration of phenol and cyclohexanone in the reaction mixture, and means for sensing temperature of the entering reaction mixture and the exiting reaction mixture at each reactor. These sampled inputs are processed in the computer by relating them to a stored anticipatory control program to provide output data for controlling the ratio of phenol to cyclohexanone and limiting the maximum reaction temperature during the hydrogenation reaction stages. The direct digital control (DDC) system controls the hydrogen pressure in each of the reactors, whereby the rate of hydrogenation in each reactor is controlled to provide a predetermined mole ratio of phenol to cyclohexanone and a predetermined maximum temperature in each reactor.

In particular, the hydrogen pressure control by the DDC control system may be described as follows. A signal in the form of air pressure, representing hydrogen pressure in the reactor, is converted by a transducer to an electric current analog, which is brought to the proper voltage for input to the computer by a resistor network. The voltage is impressed on the analog input section of the computer and is processed in digital form in a central processor section. The digital output from the central processor section is then converted to an electrical analog. The electrical analog is then reconverted to an air pressure by a transducer, and passes via a pneumatic switch to a control valve. The control valve adjusts the hydrogen feed rate and sets hydrogen pressure in the reactor within close tolerances.

The reaction conditions in each of the three reactors is shown in the following table.

TABLE 2

|  | Reactor 1 | Reactor 2 | Reactor 3 |
|---|---|---|---|
| Temperature, °C. | 176 | 167 | 158 |
| Hydrogen Pressure, psia. | 135 | 80 | 45 |
| Residence Time, Minutes | 25 | 35 | 60 |
| Mole Ratio of Phenol to Cyclohexanone | 1.0 | 0.33 | 0.05 |
| Cyclohexanone Flash, % | 0–20 | 20 | 25 |
| Catalyst Concentration, % | 2.6 | 3.5 | 7 |

With computer control, the final mole ratio of phenol to cyclohexanone is held at 0.05, within 0.5 percent variation. This is not possible with manual control of the process.

It is noteworthy for reasons of safety that the temperature in each vessel is at or below the atmospheric boiling point of the reaction mixture present in the vessel. About 24,570 parts per hour of distillate, primarily cyclohexanone, is flashed from the three vessels; this distillate is rectified to provide substantially pure cyclohexanone. The reaction mass flowing from the third reaction vessel is fed to a continuous centrifuge, wherein the catalyst is separated from the crude cyclohexanone; the catalyst is recycled in the process. The crude cyclohexanone is rectified to recover substantially pure cyclohexanone which may be combined with the cyclohexanone recovered as described above.

In this example, average yield of cyclohexanone over a one month test period is 98 percent of theory based on phenol fed to the process. Cyclohexanol is produced at a very low rate of about 610 parts per hour. At the end of the test period, the recycling catalyst contains about 0.45 percent sodium and about 0.9 percent palladium.

EXAMPLE 2

The procedure of Example 1 is followed except that the process is controlled by manual control instead of by computer control. The control operator is provided with a graphic representation of the data in Table 1, above, and the process is operated at temperatures at or below the atmospheric boiling point in each reactor. The following table shows reaction conditions in each of the three reactors.

TABLE 3

|  | Reactor 1 | Reactor 2 | Reactor 3 |
|---|---|---|---|
| Temperature, °C. | 150–180 | 150–175 | 140–165 |
| Hydrogen Pressure, psia. | 50–200 | 40–200 | 15–60 |
| Residence Time, Minutes | 10–60 | 15–75 | 30–120 |
| Mole Ratio of Phenol to Cyclohexanone | 0.4–3.0 | 0.2–1.0 | 0.01–0.4 |
| Cyclohexanone Flash, % | 0–20 | 0.14 50 | 0–50 |
| Catalyst Concentration, % | 1–5 | 1.5–8 | 3–15 |

As compared with computer control of the process, manual control is relatively erratic. However, the hydrogenation reaction is very responsive to changes in hydrogen pressure, i.e., the reaction rate increases with increased hydrogen pressure and vice versa. Surprisingly, the hydrogenation apparently follows less than first order reaction rate when the phenol conversion exceeds about 50 percent.

EXAMPLE 3

The procedure of Example 1 is followed except that the hydrogen is added in the form of a synthesis gas containing about 77 mole percent hydrogen, the remainder being nitrogen and a small amount of other inert gases. The partial pressure of hydrogen in the first reactor is maintained at 115–140 psig by the computer, the total pressure in the second reactor is maintained at about 75 psig less than the pressure in the first reactor by means of a pressure differential valve, and the total pressure in the third reactor is maintained at about 75 psig less than the pressure in the second reactor by means of a pressure differential valve. A back-pressure control valve is used to maintain the desired pressure in third reactor. Computer control of this system is relatively simple. The inert gas in the system serves to facilitate the cyclohexanone flash, which in turn helps to maintain a favorable phenol to cyclohexanone mole ratio in the reaction mixture.

We claim:

1. A computer controlled process for producing cyclohexanone by liquid phase hydrogenation of phenol in the presence of a sodium-promoted palladium-on-carbon catalyst, including a control system for controlling the ratio of phenol to cyclohexanone in the reaction mixture and limiting the maximum reaction temperature during hydrogenation reaction stages in three or more reactors in series, comprising:
   (a) generating and storing in the computer sampled data inputs from each reactor of analog representations of reactor hydrogen pressure, temperature, phenol concentration, cyclohexanone concentration, catalyst concentration, hydrogen feed rate, phenol feed rate and cyclohexanone flash rate;

(b) processing said sampled inputs in the computer by relating them to a stored anticipatory control program to provide output data for controlling the ratio of phenol to cyclohexanone and limiting the maximum reaction temperature during the hydrogenation reaction stages; and (c) controlling the ratio of phenol to cyclohexanone and limiting the maximum reaction temperature during said hydrogenation reaction stages in response to said output data from the computer, the process being further characterized in that the reaction temperature is maintained at or below the atmospheric boiling point of the reaction mixture in each reactor.

2. The process of claim 1 wherein the reaction temperature is maintained at 135° C. to 184° C. and at or below the atmospheric boiling point of the reaction mixture in each reactor.

3. The process of claim 1 wherein the catalyst is further characterized in that it is composed of palladium coated carbon particles, said carbon particles having diameters of 3 to 300 microns and a surface area of 100 to 2000 m²/gram.

4. The process of claim 1 wherein the phenol contains a small amount of an in situ promoter selected from the group consisting of sodium hydroxide, sodium carbonate and sodium phenate, said amount being 10 to 300 ppm in terms of alkali metal of said in situ promoter.

5. The process of claim 4 wherein said in situ promoter contained in said phenol is sodium hydroxide.

6. The process of claim 4 wherein said in situ promoter contained in said phenol is sodium carbonate.

7. The process of claim 4 wherein said in situ promoter contained in said phenol is sodium phenate.

8. A process for producing cyclohexanone by liquid phase hydrogenation of phenol in the presence of a sodium-promoted palladium-on-carbon catalyst at a temperature of 135° C. to 184° C., said catalyst being further characterized in that it is composed of palladium coated carbon particles, said carbon particles having diameters of 3 to 300 microns and a surface area of 100 to 2000 m²/gram, said phenol containing a small amount of an in situ promoter selected from the group consisting of sodium hydroxide, sodium carbonate and sodium phenate, said amount being 10 to 300 ppm in terms of alkali metal of said in situ promoter, including a computer controlled system for controlling the ratio of phenol to cyclohexanone in the reaction mixture and limiting the maximum reaction temperature during hydrogenation reaction stages in three or more reactors in series, comprising:

(a) generating and storing in the computer sampled data inputs from each reactor of analog representations of reactor hydrogen pressure, temperature, phenol concentration, cyclohexanone concentration, catalyst concentration, hydrogen feed rate, phenol feed rate and cyclohexanone flash rate;

(b) processing said sampled inputs in the computer by relating them to a stored anticipatory control program to provide output data for controlling the ratio of phenol to cyclohexanone and limiting the maximum reaction temperature during the hydrogenation reaction stages; and (c) controlling the ratio of phenol to cyclohexanone and limiting the maximum reaction temperature during said hydrogenation reaction stages in response to said output data from the computer, the process being further characterized in that the reaction temperature is maintained at or below the atmospheric boiling point of the reaction mixture in each reactor.

9. The process of claim 8 wherein said in situ promoter contained in said phenol is sodium hydroxide.

10. The process of claim 8 wherein said in situ promoter contained in said phenol is sodium carbonate.

11. The process of claim 8 wherein said in situ promoter contained in said phenol is sodium phenate.

12. A continuous process for producing cyclohexanone by liquid phase hydrogenation of phenol in the presence of a sodium-promoted palladium-on-carbon catalyst at a temperature of 135° C. to 184° C., said catalyst being further characterized in that it is composed of palladium coated carbon particles, said carbon particles having diameters of 3 to 300 microns and a surface area of 100 to 2000 m²/gram, said phenol containing a small amount of an in situ promoter selected from the group consisting of sodium hydroxide, sodium carbonate and sodium phenate, said amount being 10 to 300 ppm in terms of alkali metal of said in situ promoter, said hydrogenation reaction being carried out in 3 to 5 reactors, in series arrangement, wherein the mole ratio of phenol to cyclohexanone in each reactor and the reaction temperature in each reactor are correlated so that the reaction temperature approaches but does not exceed the atmospheric boiling point of the reaction mixture in each reactor, said hydrogenation reaction being controlled at least in part by adjusting the hydrogen pressure in the first reactor within the range 50–200 psig, in the second reactor within the range 40–200 psig, and in reactors 3 to 5 within the range 15 psig to a pressure of 75 psig less than the pressure in the second reactor.

* * * * *